United States Patent [19]
Meltzer

[11] Patent Number: 5,645,586
[45] Date of Patent: Jul. 8, 1997

[54] CONFORMING IMPLANTABLE DEFIBRILLATOR

[75] Inventor: Mark J. Meltzer, San Francisco, Calif.

[73] Assignee: Ventritex, Inc., Sunnyvale, Calif.

[21] Appl. No.: 272,722

[22] Filed: Jul. 8, 1994

[51] Int. Cl.$^6$ ...................................... A61F 2/00
[52] U.S. Cl. .............................. 623/11; 623/66; 607/116; 220/4.23; 220/339
[58] Field of Search ............................ 220/339, 338, 220/4.26, 4.23, 4.22, 4.27; 206/820; 623/11, 16, 24, 66; 224/224, 225; 604/20; 607/116, 129, 100–101, 154, 155

[56] References Cited

U.S. PATENT DOCUMENTS

| | | | |
|---|---|---|---|
| 733,478 | 6/1903 | Halladay | 224/225 |
| 4,693,719 | 9/1987 | Franko | 623/11 |
| 4,919,259 | 4/1990 | Beaulieu | 220/339 |
| 5,069,332 | 12/1991 | Williams et al. | 220/339 |
| 5,172,347 | 12/1992 | Masuda | 607/154 |
| 5,224,928 | 7/1993 | Sibalis et al. | 604/20 |
| 5,241,960 | 9/1993 | Anderson et al. | 607/154 |
| 5,312,442 | 5/1994 | O'Phelan | 607/5 |
| 5,328,453 | 7/1994 | Sibalis | 604/20 |
| 5,374,285 | 12/1994 | Vaiani et al. | 607/116 |
| 5,383,840 | 1/1995 | Heilman et al. | 600/17 |
| 5,385,575 | 1/1995 | Adams | 607/5 |
| 5,387,189 | 2/1995 | Gory et al. | 604/20 |

FOREIGN PATENT DOCUMENTS 9321849  11/1993  WIPO .................... 623/11

*Primary Examiner*—David Isabella
*Assistant Examiner*—Bruce E. Snow
*Attorney, Agent, or Firm*—Steven M. Mitchell; Mark J. Meltzer

[57] ABSTRACT

An implantable device, such as a defibrillator, has a conforming housing that is adapted to follow to the contours of the patient's body at a device implantation site, while complying with pressures applied to the patient's body and with body flexion. In one form of the invention, the device housing is articulated at one or more hinge locations to provide a segmented housing that conforms to an implantation site through movement about the hinge axis. Another embodiment of the invention provides a flexible housing that surrounds a flex-circuit assembly.

5 Claims, 5 Drawing Sheets

CONFORMING IMPLANTABLE DEFIBRILLATOR

BACKGROUND OF THE INVENTION

1. Technical Field

The present invention relates to implantable medical devices. More particularly, the present invention relates to an implantable medical device that is adapted to conform to the contour of an implantation site and/or to flex in compliance with movement at such implantation site.

2. Description of the Prior Art

Certain medical devices, such as pulse generators, including cardiac pacemakers and defibrillators, are implanted within a patient's body to monitor patient conditions and/or to administer cardiac arrhythmia therapy as necessary. Advances in microelectronic technology have allowed the manufacture of implantable medical devices that are increasingly sophisticated in their ability to diagnose, counteract, and report critical patient events, such as cardiac arrhythmia.

Prior art implantable defibrillators typically have been relatively large, such that it was necessary to implant the device in the patient's abdominal cavity. Such implantation requires somewhat complex and time consuming surgery and sometimes results in patient discomfort.

K. Anderson, T. Adams, M. Kroll, *Defibrillation Pulse Generator*, U.S. Pat. No. 5,241,960 (7 Sep., 1993) discloses a pulse generator adapted for implantation in the pectoral region of a patient's body. The device is sealed in a housing structure that has a contoured periphery and that is constructed of a biocompatible material. The device and housing are smaller in size than conventional defibrillators, and the device therefore delivers lower output voltage. However, the proximity of the device to the patient's heart, i.e. in the patient's pectoral muscle region, is thought to allow the device to deliver a more effective shock to the patient's heart than conventional defibrillators.

Although the form factor of implantable medical devices is decreasing (e.g. Anderson et al, discussed above), the implantation and siting of such devices within the human body is still problematic for at least the following reasons: the bulk of such devices displaces the patient's flesh, thereby creating a skin dislocation that is both unsightly and that may protrude sufficiently from the otherwise continuous surface of the patient's skin to expose the device in such way that may be subjected to impact that can damage the device; situating such devices within the patient's body, rather than under the surface of the patient's skin may make access to the device for installation, service, or replacement an unnecessarily invasive surgical procedure that is expensive, and both stressful and painful to the patient; and because such devices are fashioned as packaged electronic assemblies without substantial regard to the contour of or flexion within or about the patient's body, they may cause patient discomfort.

Although it is known to reduce device volume and weight, such that low profile implantable devices may be made, such devices are packaged as rigid assemblies that do not conform to, or comply with, the patient's body. Thus, while smaller devices are produced, such devices may still be somewhat obtrusive and uncomfortable, and may interfere with the patient's normal day-to-day activities. Additionally, there is a possibility that the device will irritate the implantation site, resulting in medical complications. Further, in the case of a pulse generator, interruption to device operation, for example if the device is damaged, can have dire consequences for the patient.

Accordingly, improvements must still be made in fitting implantable devices to the patient's body.

SUMMARY OF THE INVENTION

The invention provides an implantable device, such as a defibrillator, having an articulated housing that is adapted to conform to the contours of the patient's body at the device implantation site; and that is also adapted to comply with pressures applied to the patient's body and body flexion, such that having the device is a relatively unobtrusive during low impact exercise. In one form of the invention, the device housing is articulated at one or more hinge locations to conform to an implantation site through movement about the hinge axis. Another embodiment of the invention provides a flexible housing that surrounds a flex-circuit assembly.

In particular, a first embodiment of the invention provides a housing for an implantable medical device that includes at least two discrete, cooperating housing segments constructed of a biocompatible material, such as silicone rubber, Teflon®, or polyurethane. The segments are positioned such that an edge of one segment is proximate to and coaxial with an edge of the other segment, and such that the segments define an integrated, articulated housing structure having a contoured periphery. The segments are adapted to pivot at at least one hinge axis located between the segments. Thus, the housing is adapted to conform to the contour of an implantation site and/or to flex in compliance with movement at said implantation site through pivotal movement of the segments, one relative the other, about the hinge axis.

A second embodiment of the invention provides a housing for an implantable medical device in the form of a flexible enclosure that is constructed of a biocompatible material. The housing is adapted to surround and seal a flex-circuit assembly. Thus, the housing and the assembly contained therein yield elastically when force is applied thereto, and thereby comply with the contour of a device implantation site and/or flex in compliance with movement at or relative to the implantation site.

DETAILED DESCRIPTION OF THE INVENTION

The present invention provides a conforming, highly compliant housing for an implantable medical device, such as a defibrillator. For purposes of the discussion herein, when the housing is described as "conforming", the housing is said to follow the shape, outline, or contour at the implantation site; and when the housing is described as "compliant", the housing is said to yield elastically when force is applied thereto, i.e. the housing is flexible (*Webster's Ninth New Collegiate Dictionary*, Merriam-Webster, Inc., 1983).

Figure 1:
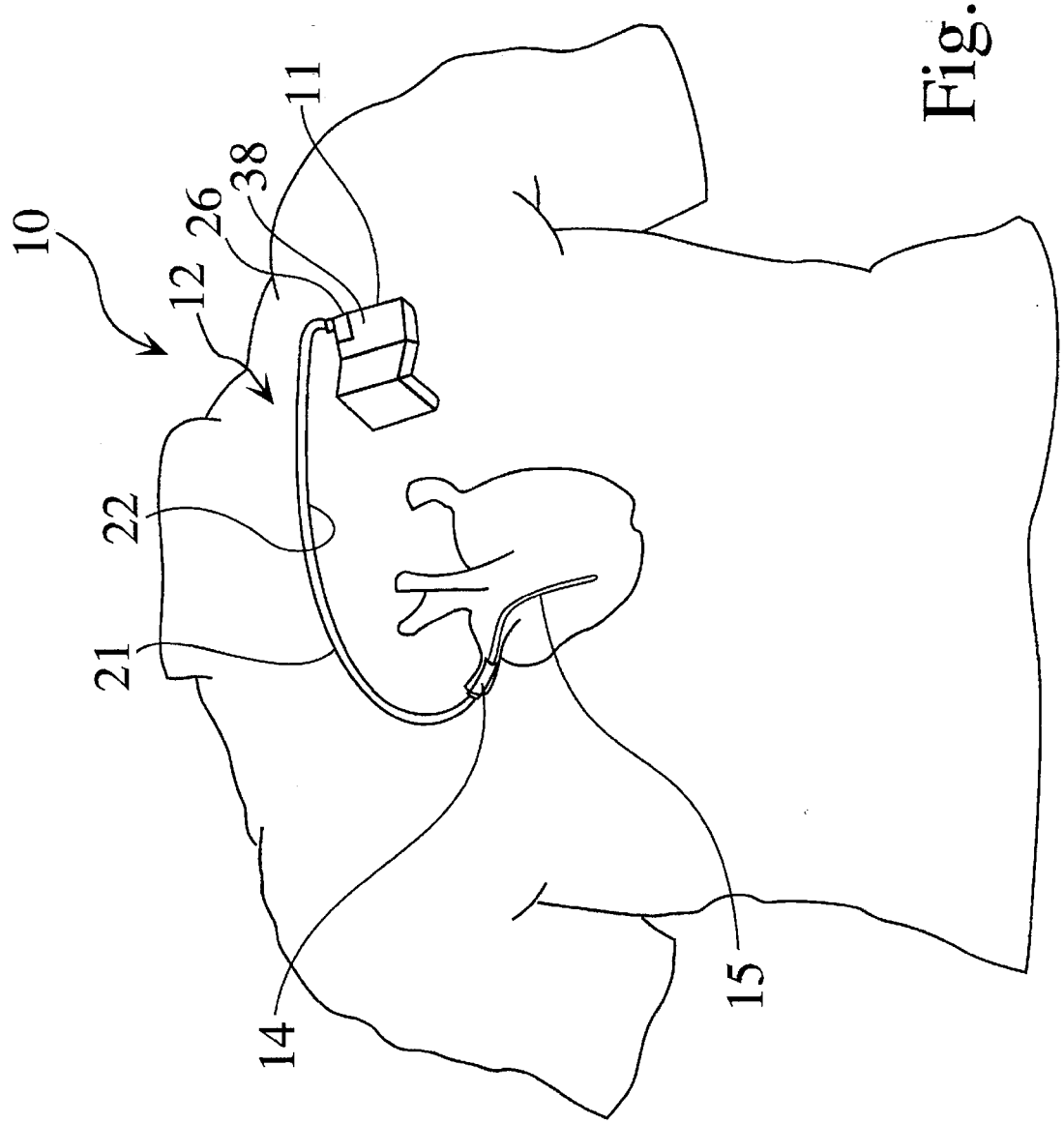
FIG. 1 is a frontal plan view of a conforming implantable device that is situated in the pectoral position of a patient according to the invention.

FIG. 1 shows an implantable device 11 according to the invention, that is implanted in the pectoral region 12 of the chest of a patient 10. The device housing 38 includes one or more ports 26 that allow connection of the device to various sensing and defibrillation leads, as is known in the art. For example, the leads 21 and 22 are shown extending from the device to the electrodes 14 and 15 which are positioned, respectively, in to the superior venacava and the right ventricle of the patient's heart. The specific complement and location of electrodes is determined by the application in which the device is used. It should be appreciated that the invention is intended for use in other applications, in addition to the cardiac applications that are discussed herein for purposes of example.

Figure 2:
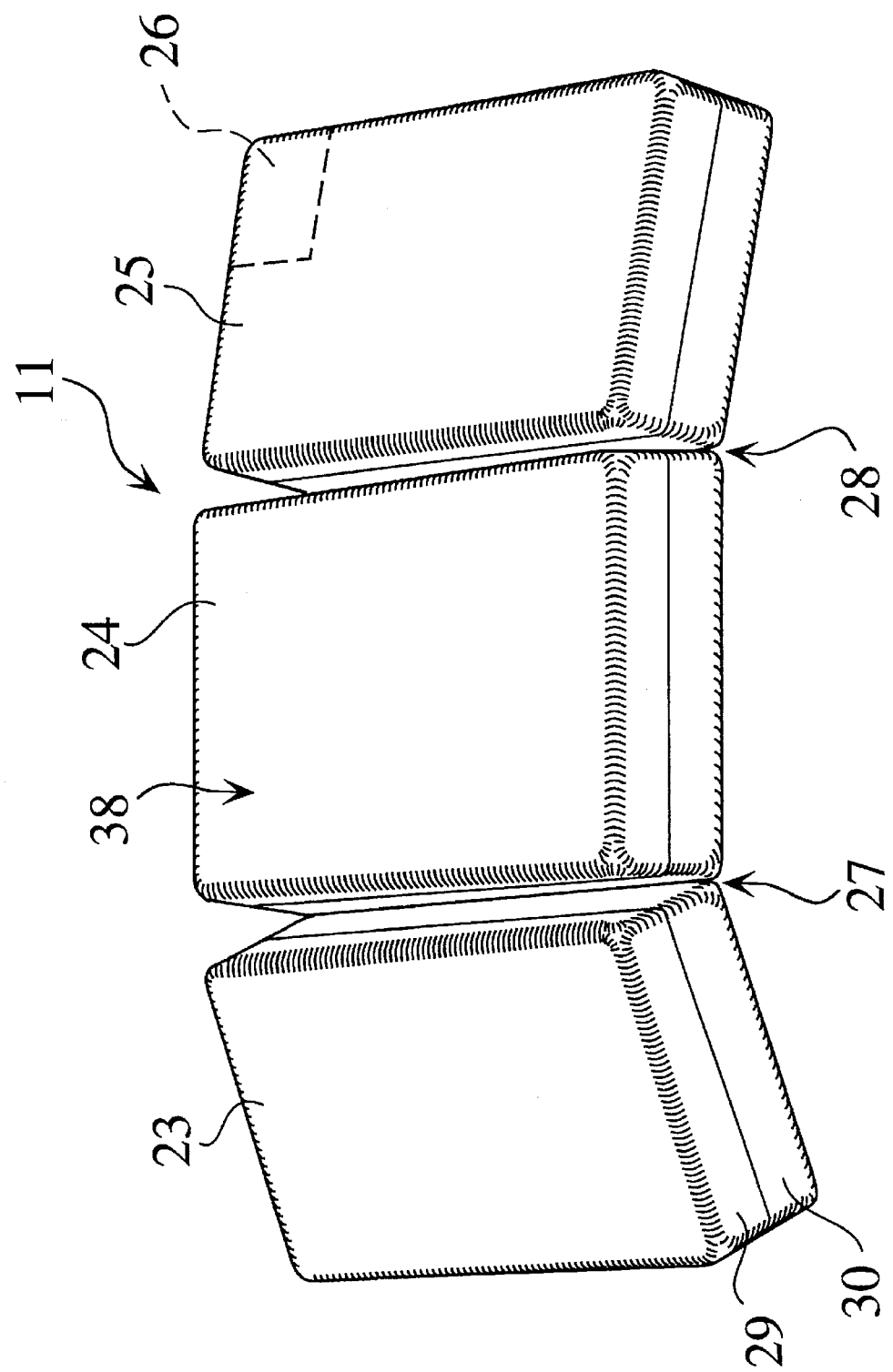
FIG. 2 is a perspective view of an articulated implantable device having a plurality of hinged locations according to the invention.

FIG. 2 shows the device housing 38 in perspective. The housing shown in FIG. 2 is articulated and includes three segments 23, 24, and 25 that are interconnected at, and pivot about, hinge axes 27, 28. The hinge axes are constructed in such manner that segments may pivot about each axis, one relative to the other without compromising the integrity of the enclosure seal. Such pivotal movement allows the housing to assume the contour of the device implantation site, for example the housing segments may be pivoted such that the device assumes an overall curved shape that corresponds to the patient's pectoral region.

Figure 3:
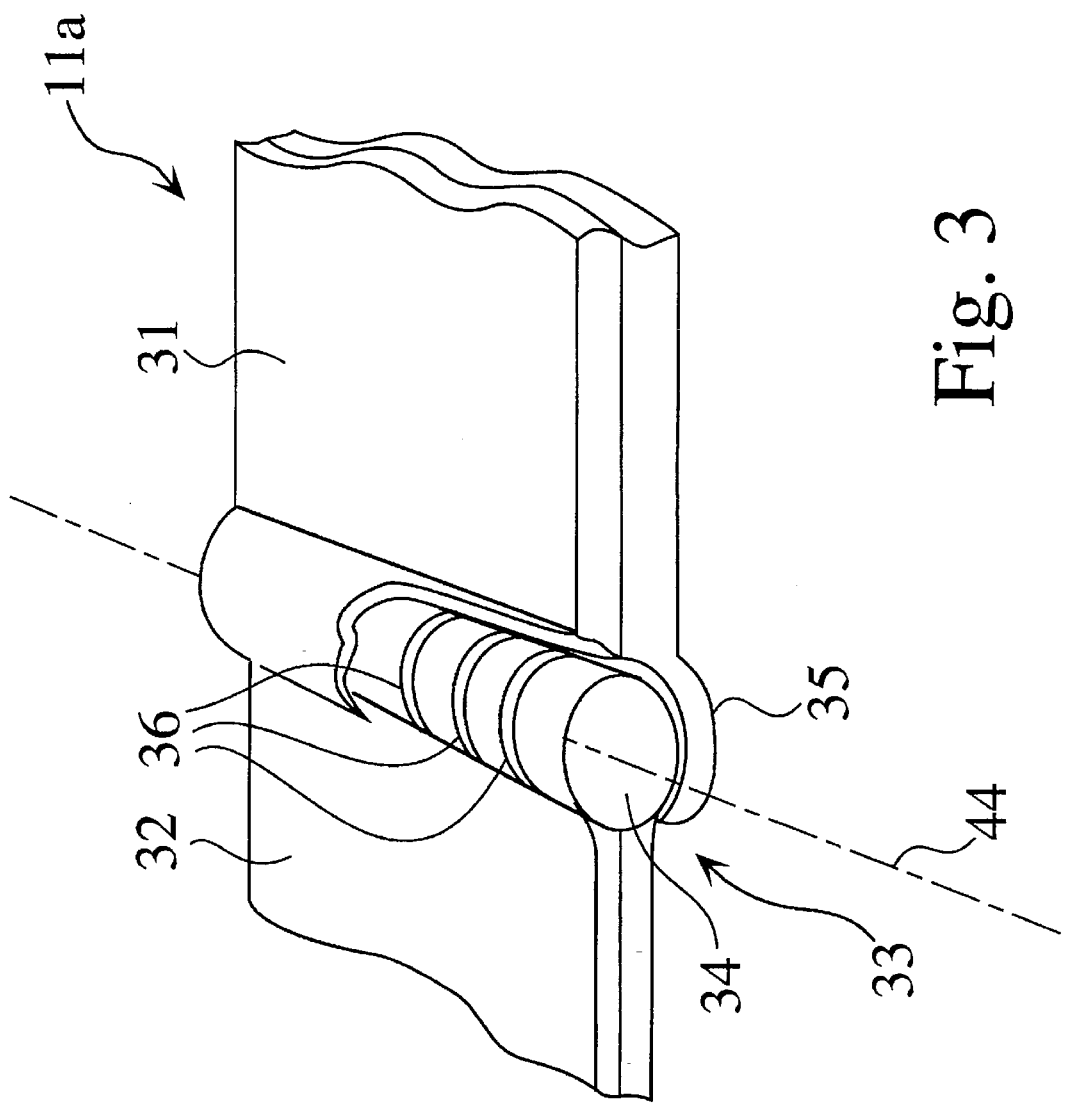
FIG. 3 is a perspective detail view of a hinge arrangement for an articulated implantable device according to the invention.

Additionally, the hinge axis provides a flexible electrical interconnection between various segments of an articulated electronic assembly contained within the housing. The flexible interconnection may be a set of complementary contacts (as shown in FIG. 3), or it may be a flexible interconnect, such as a ribbon cable or a flex-circuit.

Each segment of the enclosure is composed of mating half shells, e.g. for the segment 23, two half shells 29, 30 are provided that are adapted for sealing engagement, one half shell with the other. Typically such engagement is accomplished by welding the half shells together to form an hermetic seal. Alternatively, engagement of the two half shells may be accomplished by forming one half shell with a flange and the other half shell with a complementary channel. Any other known mechanism may also be used, including the use of various adhesive. The housing may also be formed as a solid assembly having a sealable opening, for example at an end, through which the electronic assembly may be inserted.

The housing is constructed of a biocompatible material, such as titanium or stainless steel. The connector member is also constructed of a biocompatible material, such as a biocompatible polymeric composition (e.g. Teflon® or silicone rubber).

The enclosure is constructed with sufficient internal capacity to contain the various assemblies that comprise the implantable device. The actual construction and operation of an implantable medical device of the type for which the invention herein would find ready application, for example a defibrillator, is well known. See, for example B. Pless, P. Ball, E. Fain, *Cardiac Therapy Method*, U.S. Pat. No. 4,969,465 (13 Nov., 1990); B. Pless, M. Sweeney, R. Winkle, A. Nathan, *Method For Combined Cardiac Pacing And Defibrillation*, U.S. Pat. No. 5,048,521 (17 Sep., 1991).

FIG. 3 is a perspective detail view of a hinge arrangement 33 for an articulated implantable device 11a according to a first embodiment of the invention. In the figure, two housing segments 31, 32 are shown engaged, one with the other, for pivotal movement about a hinge axis 44. In this embodiment of the invention, one housing segment 32 terminates in an elongated, transverse cylinder 34 that is adapted for complementary engagement with a terminal portion of a second housing segment 31. The terminal portion of the second housing segment is an elongated, transverse channel 35 that receives and partially surrounds the cylinder shaped terminal portion of the first segment 32. The two segments are therefore adapted to pivot, one relative to the other, while maintaining the integrity of the housing seal at the pivot location. It will be appreciated that the actual number of housing segments, as well as the actual manner in which the housing segments are joined for pivotal movement, may take many forms, depending upon the application to which the invention is put.

The figure shows the hinge portion configured in partial section, exposing a series of parallel conductors 36. The conductors are arranged for sliding contact with a complementary set of conductors, such that pivotal movement of the segments, one relative to the other, rotates the conductors 36 in sliding contact with the complementary set of conductors (not shown) and thus maintains reliable electrical communication between the electrical assemblies contained within each of the housing segments. Thus, it is expected that in some applications of the invention, the electrical assemblies that compose the device will be themselves segments and interconnected at the hinge axes by an arrangement, such as discussed above, or by a ribbon cable or flex circuit. In other applications, a unitary electronic assembly may be provided that is formed on a flex circuit, such that the assembly itself flexes at the hinge axes. One advantage of such arrangement would be to reduce or eliminate the possibility of interconnect failure associated with a cable interconnect or sliding contact arrangement.

Figure 4:
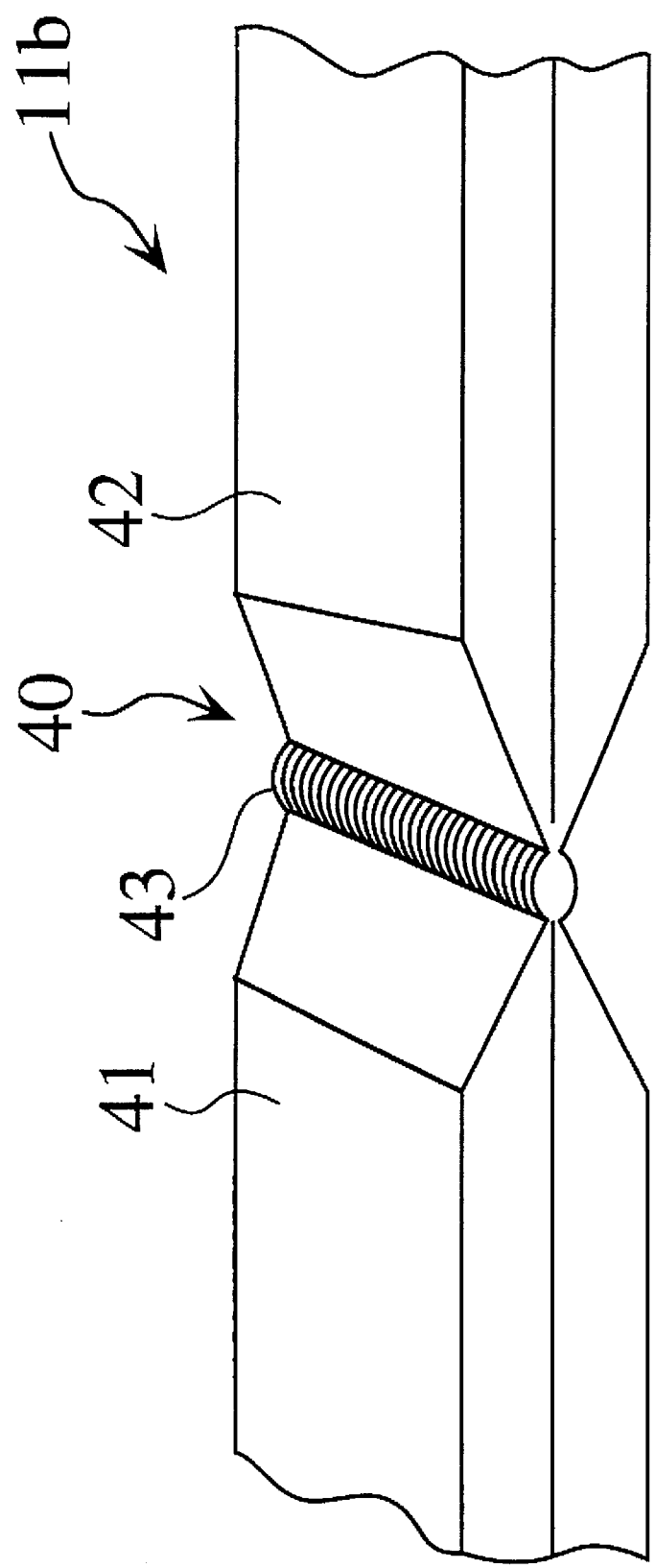
FIG. 4 is a perspective detail view of another hinge arrangement for an articulated implantable device according to the invention.

FIG. 4 is a perspective detail view of another hinge arrangement 40 for an articulated implantable device 11b according to the invention. In this device, the hinge arrangement 40 uses an encapsulated interconnect cable 43, such as a ribbon cable, to electrically and mechanically couple two housing segments 41, 42 together for pivotal movements, one segment relative to the other. Thus, the electrical interconnect also provides a flexible mechanical interconnect for the various housing segments. The entire housing may be coated with a biocompatible polymer, such as silicone rubber, to seal the hinge thus formed, or the housing segments may have individual seals at the point where the interconnect emerges therefrom.

Figure 5:
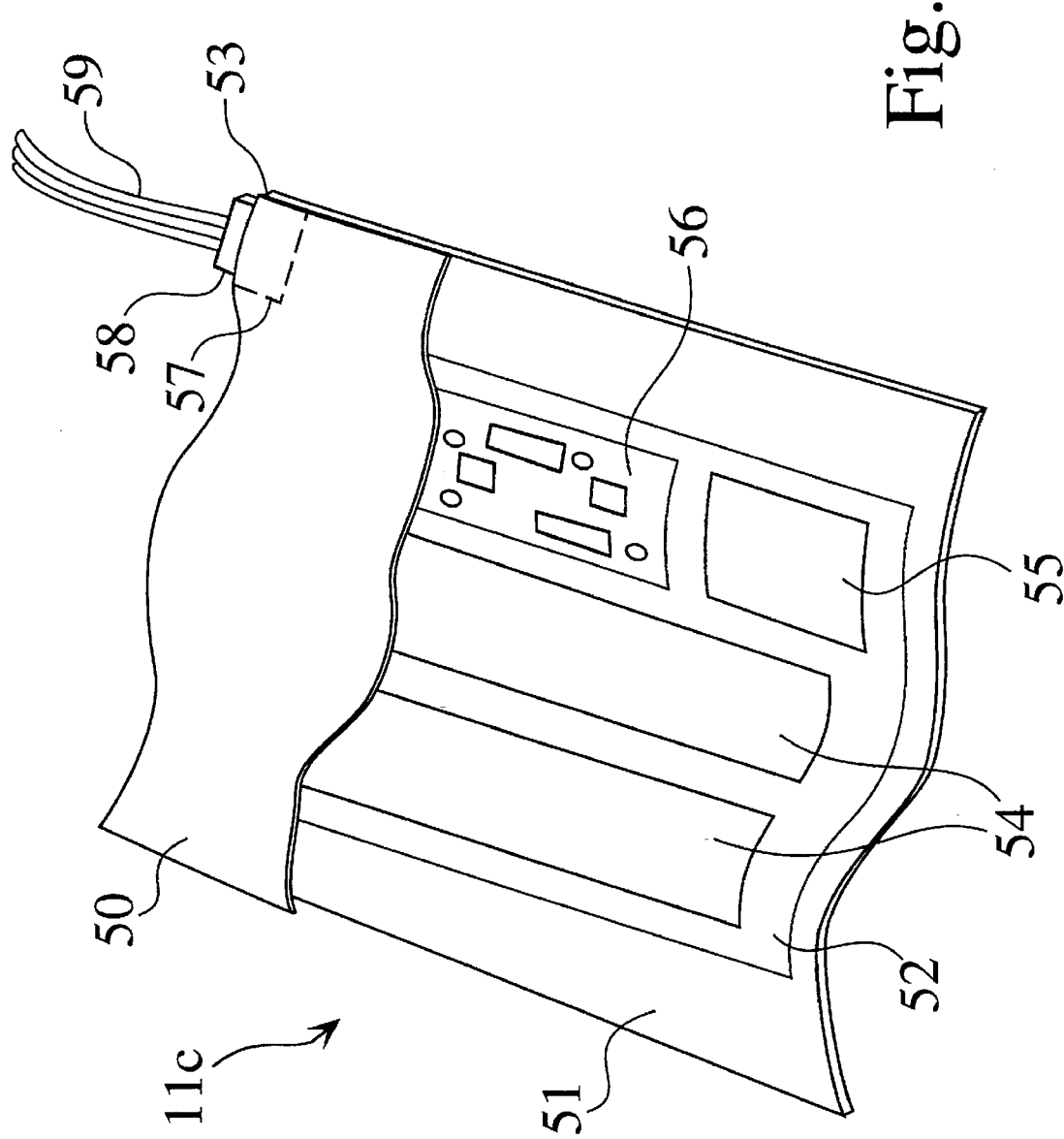
FIG. 5 is a perspective view of an implantable device that is fabricated on a flexible circuit substrate and that has a highly compliant flexible housing according to the invention.

FIG. 5 is a perspective view of an implantable device 11c that is fabricated on a flexible circuit substrate 52 and that has a highly compliant flexible housing 50, 51 according to the invention. In this embodiment of the invention, a flexible housing is provided having a flexible sleeve composed of two pliable, biocompatible members 50, 51 that are laminated at their edges 53 to form a sealed enclosure for a flex-circuit assembly 52. Various components, e.g. high voltage capacitors 54, a battery 55, and a logic assembly 56 are shown mounted to the flex-circuit. A connector port 57 is shown receiving a mating lead connector 58 that couples various electrode to the device via a lead 59. The assembly may be packed in a non-toxic foam or other padding, or it may be slightly filled with an inert fluid, to cushion the internal components of the device.

This embodiment of the invention is especially compliant, that is it yields under pressure. As such, vigorous exertion by the patient, in which the patient's muscles are repeatedly flexed, or where there is contact between the patient and other persons or objects, the device housing complies with the underlying contour of the patient's body at the implantation site. In this way, the implantation site has a more natural less stressful reaction to impact and more evenly distributes the force of such impact to the patient and through the device.

Although the invention is described herein with reference to the preferred embodiment, one skilled in the art will readily appreciate that other applications may be substituted for those set forth herein without departing from the spirit and scope of the present invention. Accordingly, the invention should only be limited by the claims included below.

I claim:

1. A housing for an implantable defibrillator for implantation in the pectoral region of a patient, the housing comprising:

at least two discrete, cooperating housing segments constructed of a biocompatible material, the segments positioned such that an edge of one segment is proximate to and coaxial with an edge of the other segment, and such that the segments define an integrated, articulated housing structure having a contoured periphery, wherein the segments are adapted to pivot at at least one hinge axis located between said segments, whereby the housing is configured to conform to the contour of an implantation site in the pectoral region of the patient's chest and to flex in compliance with movement at said implantation site through pivotal movement of said segments, one relative the other, about said hinge axis.

2. The housing of claim 1, wherein said at least two housing segments are engaged, one with the other, for pivotal movement about said hinge axis, wherein one housing segment terminates in an elongated, transverse cylinder that is adapted for complementary engagement with a terminal portion of a second housing segment; and wherein a terminal portion of said second housing segment is an elongated, transverse channel that receives and partially surrounds said cylinder shaped terminal portion of said first segment.

3. The housing of claim 2, further comprising:

a first set of parallel conductors that are adapted for sliding contact with a second, complementary set of conductors, such that pivotal movement of said first and second housing segments, one relative to the other, rotates said first set of conductors in sliding contact with said second set of conductors; wherein electrical communication is maintained between each of the housing segments.

4. The housing of claim 1, wherein said first and second segments are electrically and mechanically interconnected by either of a ribbon cable and a flex-circuit.

5. The housing of claim 1, wherein each housing segment is comprised of mating first and second segment half shells.

* * * * *